(12) United States Patent
Uchibori

(10) Patent No.: US 7,666,142 B2
(45) Date of Patent: Feb. 23, 2010

(54) ULTRASOUND DOPPLER DIAGNOSTIC APPARATUS AND IMAGE DATA GENERATING METHOD

(75) Inventor: Takanobu Uchibori, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 775 days.

(21) Appl. No.: 10/899,036

(22) Filed: Jul. 27, 2004

(65) Prior Publication Data
US 2005/0080329 A1    Apr. 14, 2005

(30) Foreign Application Priority Data
Jul. 29, 2003    (JP) ............................. 2003-203088

(51) Int. Cl.
*A61B 8/00* (2006.01)
(52) U.S. Cl. ................... 600/453; 600/437; 382/128; 73/584; 367/157
(58) Field of Classification Search ............. 600/437, 600/453–458; 382/128, 173, 260, 263–275, 382/280; 267/157, 140; 73/584, 610, 618, 73/625, 628, 632
See application file for complete search history.

(56) References Cited
U.S. PATENT DOCUMENTS

| | | | | |
|---|---|---|---|---|
| 5,287,753 A * | 2/1994 | Routh et al. | ............. | 73/861.25 |
| 5,485,844 A * | 1/1996 | Uchibori | ................... | 600/455 |
| 5,647,366 A * | 7/1997 | Weng | ......................... | 600/453 |
| 5,868,676 A * | 2/1999 | McCabe et al. | ............. | 600/454 |
| 5,935,074 A * | 8/1999 | Mo et al. | ................... | 600/454 |
| 6,030,345 A * | 2/2000 | Wang | ......................... | 600/454 |
| 6,050,948 A * | 4/2000 | Sasaki et al. | ................ | 600/453 |
| 6,142,943 A | 11/2000 | Mo et al. | | |
| 6,296,612 B1 * | 10/2001 | Mo et al. | ................... | 600/455 |
| 6,663,566 B2 * | 12/2003 | Pan et al. | ................... | 600/454 |
| 6,733,452 B2 * | 5/2004 | Bae et al. | ................... | 600/443 |
| 6,733,454 B1 * | 5/2004 | Bakircioglu et al. | ........ | 600/453 |
| 2006/0084873 A1 | 4/2006 | Baba et al. | | |

\* cited by examiner

*Primary Examiner*—Brian Casler
*Assistant Examiner*—Parikha S Mehta
(74) *Attorney, Agent, or Firm*—Oblon, Spivak, McClelland, Maier & Neustadt, L.L.P.

(57) ABSTRACT

An ultrasonic Doppler diagnostic equipment comprising a spectrum measurement unit which measures a Doppler spectrum, a decision unit which determines processing conditions of an average process on the basis of power values of spectral components in the Doppler spectrum, an average process unit which performs the average process of the Doppler spectrum on the basis of the processing conditions determined by the decision unit, and a display unit which displays a Doppler spectral image on the basis of the Doppler spectrum subjected to the average process by the average process unit. According to the configuration, the ultrasonic Doppler diagnostic equipment can improve discontinuities in those spectral components of small power values which are susceptible to interference noise, in the Doppler spectral image, and it can generate image data of high resolution.

12 Claims, 10 Drawing Sheets

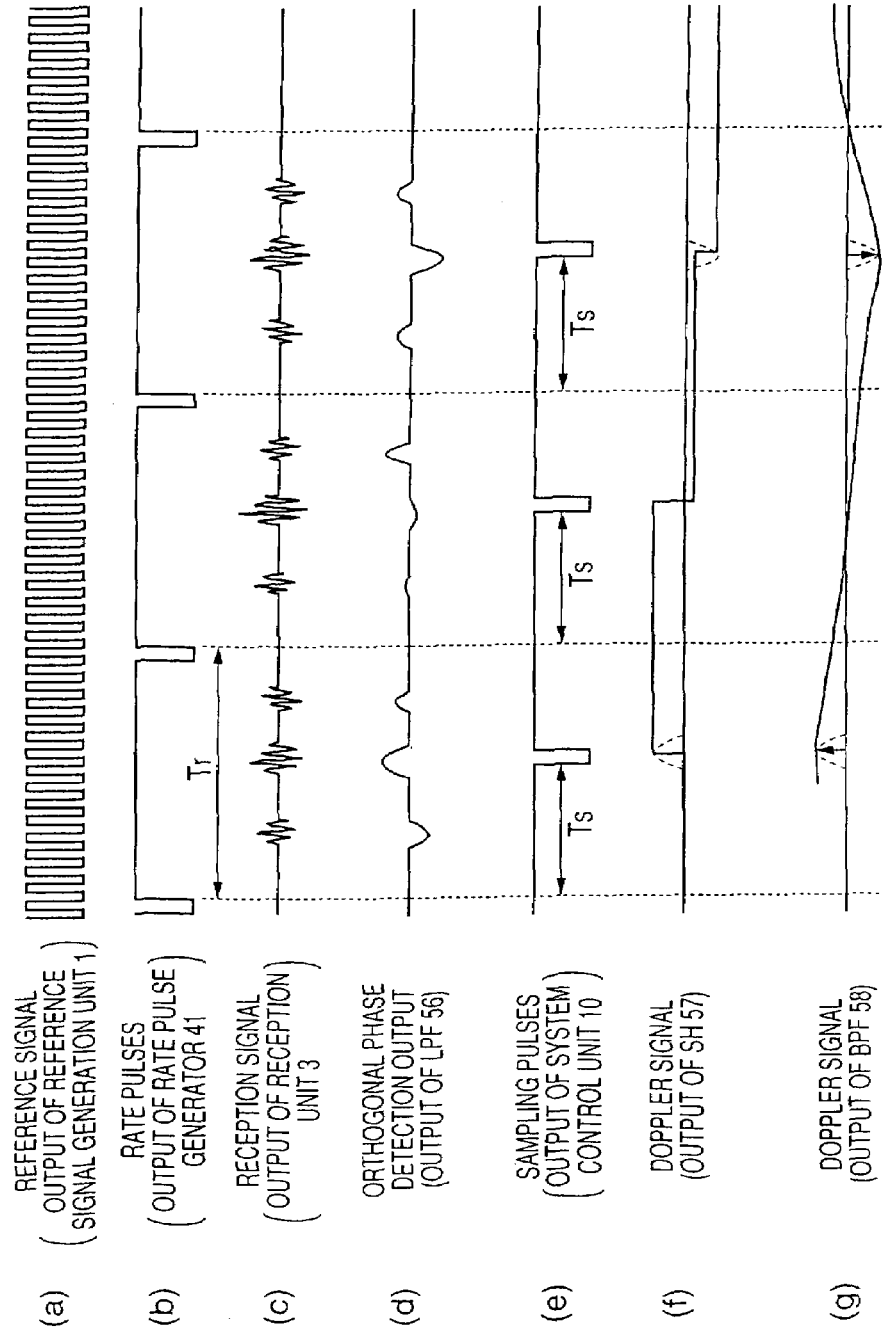

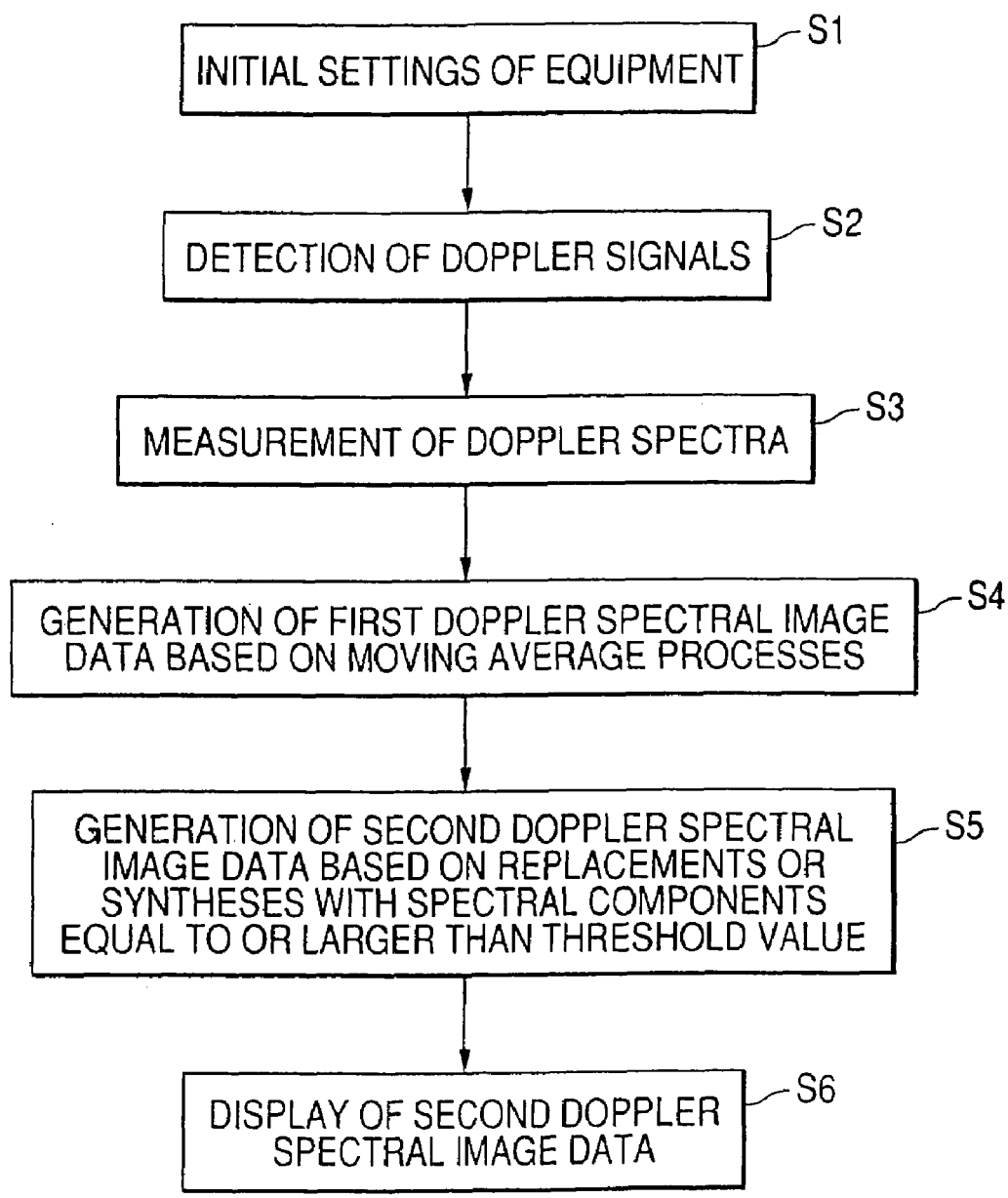

ULTRASOUND DOPPLER DIAGNOSTIC APPARATUS AND IMAGE DATA GENERATING METHOD

BACKGROUND OF THE INVENTION

1. Field of the Invention

The present invention relates to an ultrasonic Doppler diagnostic equipment and an image data generation method wherein the flow velocity information of a blood flow within a living body, the movement information of a tissue, etc. are measured by utilizing the Doppler effect of ultrasounds.

2. Description of the Related Art

An ultrasonic diagnostic equipment is such that ultrasonic pulses which have been generated from piezoelectric transducers built in an ultrasonic probe are radiated into a patient, and that ultrasonic reflected waves generated by the difference of the acoustic impedance of a patient tissue are received by the piezoelectric transducers and then displayed on a monitor. Such a diagnostic method is extensively employed for the functional diagnoses and morphological diagnoses of the various internal organs of the living body because a two-dimensional image can be easily observed in real time by the simple operation of merely bringing the ultrasonic probe into touch with the surface of the body. An ultrasonic diagnostic method which obtains in-vivo information on the basis of reflected waves from a tissue or blood corpuscles within a living body has made rapid progress owing to the great technological developments of two methods; an ultrasonic pulse echo method and an ultrasonic Doppler method. A B-mode image and a color Doppler image which are obtained using the technologies, are indispensable to ultrasonic image diagnoses of today.

On the other hand, a Doppler spectrum method is a method which quantitatively and precisely obtains a blood flow velocity at any desired position of a patient. In the Doppler spectrum method, ultrasounds are transmitted to and received from the same part of the patient at regular intervals a plurality of times, and ultrasonic reflected waves from mobile reflectors such as blood corpuscles are subjected to orthogonal phase detection by employing a reference signal whose frequency is substantially equal to the resonance frequency of piezoelectric transducers used for the ultrasound transmissions and receptions, thereby to detect Doppler signals. Herein, a Doppler spectrum is calculated in such a way that Doppler signals at the desired part is extracted from among the detected Doppler signals by a range gate, and that the extracted Doppler signals are further subjected to an FFT (Fast-Fourier-Transform) analysis.

Doppler spectra are continuously calculated for Doppler signals obtained from the desired part of the patient by such steps, and the plurality of calculated Doppler spectra are successively arrayed, thereby to generate so-called "Doppler spectral image data". By the way, in general, the setting of the range gate is performed under the observation of a B-mode image in order to confirm that the range gate is precisely set at the desired observation part in the patient. On this occasion, the position of the range gate is displayed on the B-mode image.

An example of a Doppler spectral image is shown in FIG. 1. (a) on the left side of FIG. 1 shows a Doppler spectrum obtained by an FFT analysis, in which the axis of ordinates represents a Doppler frequency, while the axis of abscissas represents the magnitude (termed "power value" below) of the spectrum. Besides, (b) on the right side of FIG. 1 shows the temporal variation of the Doppler spectrum, in which the axis of ordinates is set at the Doppler frequency, while the axis of abscissas is set at time. The power of the spectrum is expressed in terms of an intensity or brightness.

Meanwhile, it has heretofore been known that random interferences occur among reflected waves from mobile reflectors within a patient, and that interference noise (speckle noise) is consequently generated in a Doppler spectral image. More specifically, as shown in (a) of FIG. 1, a calculated Doppler spectrum 151 (solid line) exhibits unevenness ascribable to the interference noise, with respect to a true Doppler spectrum 152 (broken line). Therefore, a discontinuous pattern ascribable to the influence of the interference noise is displayed also in (b) of FIG. 1 showing the temporal variation of the Doppler spectrum, and it becomes difficult to precisely measure the temporal variations of a blood flow velocity, etc. The influence of such interference noise is conspicuous in a case where the power value, namely, S/N ratio of a spectral component is small. Accordingly, in a case where the maximum blood flow velocity is measured by tracing the maximum frequency component 153 of the spectrum, precise automatic tracing or manual tracing becomes difficult. As another problem, especially in the case of the manual tracing, a long time is expended on the tracing, to increase a burden on an operator who performs the tracing.

In order to cope with such problems, there has been proposed a method wherein the interference noise is reduced by taking moving averages in a time direction in units of the individual frequency components of a Doppler spectrum (refer to, for example, JP-A-6-327672).

According to the method stated in the patent document, the influence of the interference noise is relieved, so that the edge parts of the maximum frequency component, etc. in the Doppler spectrum can be displayed continuously and smoothly, and a visuality in the case of performing the tracing is enhanced. Since, however, the moving average in each individual frequency component of the Doppler spectrum needs to be taken for a comparatively long time period for the purpose of attaining such an advantage, a sharpness on a Doppler spectral image degrades drastically. In particular, a subtle variation in the time direction or in a frequency direction, at a near-mean-frequency component having a large power value, has heretofore been deemed effective as diagnostic information, but the method in the patent document becomes difficult of sharply displaying the temporal variation of such a near-mean-frequency component.

SUMMARY OF THE INVENTION

The present invention has been made in view of the above problems, and has for its object to provide an ultrasonic Doppler diagnostic equipment and an image data generation method which can improve a discontinuity at a spectral component of small power value as is susceptible to interference noise in a Doppler spectral image, and which can display a subtle variation in a time direction or a frequency direction, for a spectral component of comparatively large power value.

In order to solve the problems, the ultrasonic Doppler diagnostic equipment according to the invention comprises a transmission/reception unit which transmits and receives ultrasounds to and from a patient; a Doppler signal detection unit which detects Doppler signals at a desired range gate position, from reception signals obtained by the transmission/reception unit; a spectrum measurement unit which measures a Doppler spectrum on the basis of the Doppler signals detected by the Doppler signal detection unit; a decision unit which determines processing conditions of an average process on the basis of power values of spectral components in the Doppler spectrum measured by the spectrum measurement unit; an average process unit which performs the average process of the Doppler spectrum on the basis of the processing conditions determined by the decision unit; and a display unit which displays a Doppler spectral image on the basis of the Doppler spectrum subjected to the average process by the average process unit.

Preferably, the decision unit determines the processing conditions so that the average process may intensity at a part of low power values than at a part of high power values, and/or the average process unit performs a moving average process in at least one of a time axis direction and a frequency direction, for the spectral components in the Doppler spectrum.

Besides, in order to solve the problems, the ultrasonic Doppler diagnostic equipment according to the invention comprises an ultrasonic probe which has piezoelectric transducers for transmitting and receiving ultrasounds to and from a patient; a transmission/reception unit which transmits and receives electric signals to and from the piezoelectric transducers; a Doppler signal detection unit which detects Doppler signals at a desired range gate position, from the reception signals obtained by the transmission/reception unit; a spectrum measurement unit which measures a Doppler spectrum on the basis of the Doppler signals detected by the Doppler signal detection unit; a threshold value setting unit which sets a threshold value for power values of spectral components in the Doppler spectrum measured by the spectrum measurement unit; an average process unit which performs an average process for the spectral components of small power values selected on the basis of the threshold value set by the threshold value setting unit, from among the spectral components in the Doppler spectrum measured by the spectrum measurement unit; an image data generation unit which generates Doppler spectral image data through component processing of mean spectral components subjected to the average process by the average process unit and the spectral components of large power values not subjected to the average process; and a display unit which displays the Doppler spectral image data.

In addition, in order to solve the problems, the ultrasonic Doppler diagnostic equipment according to the invention comprises an ultrasonic probe which has piezoelectric transducers for transmitting and receiving ultrasounds to and from a patient; a transmission/reception unit which transmits and receives electric signals to and from the piezoelectric transducers; a Doppler signal detection unit which detects Doppler signals at a desired range gate position, from the reception signals obtained by the transmission/reception unit; a spectrum measurement unit which measures a Doppler spectrum on the basis of the Doppler signals detected by the Doppler signal detection unit; a threshold value setting unit which sets a threshold value for power values of spectral components in the Doppler spectrum measured by the spectrum measurement unit; an average process unit which performs an average process for the spectral components in the Doppler spectrum measured by the spectrum measurement unit; a first image data generation unit which generates first Doppler spectral image data by employing mean spectral components subjected to the average process by the average process unit; a second image data generation unit which generates second Doppler spectral image data by selecting the spectral components of large power values on the basis of the threshold value set by the threshold value setting unit, from among the spectral components in the Doppler spectrum measured by the spectrum measurement unit, and performing component processing of the selected spectral components and the mean spectral components of the first Doppler spectral image data corresponding to the selected spectral components; and a display unit which displays the second Doppler spectral image data.

Further, in order to solve the problems, the ultrasonic Doppler diagnostic equipment according to the invention consists in comprising an ultrasonic probe which has piezoelectric transducers for transmitting and receiving ultrasounds to and from a patient; a transmission/reception unit which transmits and receives electric signals to and from the piezoelectric transducers; a Doppler signal detection unit which detects Doppler signals at a desired range gate position, from the reception signals obtained by the transmission/reception unit; a spectrum measurement unit which measures a Doppler spectrum on the basis of the Doppler signals detected by the Doppler signal detection unit; a threshold value setting unit which sets a threshold value for power values of spectral components in the Doppler spectrum measured by the spectrum measurement unit; a first average process unit which performs an average process for the spectral components in the Doppler spectrum measured by the spectrum measurement unit; a first image data generation unit which generates first Doppler spectral image data by employing first mean spectral components subjected to the average process by the first average process unit; a second average process unit which performs an average process having an average interval shorter than that of the average process based on the first average process unit, for the spectral components in the Doppler spectrum measured by the spectrum measurement unit; a second image data generation unit which generates second Doppler spectral image data by selecting second mean spectral components of large power values on the basis of the threshold value set by the threshold value setting unit, from among the second mean spectral components subjected to the average process by the second average process unit, and performing component processing of the selected second mean spectral components and the first mean spectral components of the first Doppler spectral image data corresponding to the second mean spectral components; and a display unit which displays the second Doppler spectral image data.

The synthesis processing in the second image data generation unit should desirably be either of replacement processing and weighted addition processing.

Besides, the first average process unit and the second average process unit should desirably subject the first spectral components and the second spectral components to moving average processes in at least one of a time axis direction and a frequency direction, respectively.

In addition, the threshold value setting unit can be preferably configured so as to set the threshold value for the power values of the spectral components in the Doppler spectrum, on the basis of ultrasonic data collection conditions.

More preferably, the threshold value setting unit may well be configured so as to set the threshold value for the power values of the spectral components in the Doppler spectrum, on the basis of at least either of an equipment gain and an effective aperture of the ultrasonic probe.

Alternatively, the threshold value setting unit can also be configured so as to detect a noise region from the Doppler spectral image data generated by the image data generation means, and to set the threshold value on the basis of spectral data of the noise region.

On this occasion, the threshold value setting unit may more preferably obtain a noise level at each time by regarding a predetermined region of the Doppler spectral image as the noise region, and then set the threshold value from a mean noise level with such noise levels averaged in a time direction, or it may well divide the Doppler spectral image into a blood flow region and a noise region by auto-tracing, then obtain a level of the noise region at each time, and thereafter set the threshold value from a mean noise level with such noise levels averaged in a time direction.

Meanwhile, in order to solve the problems, the image data generation method according to the invention consists in comprising a detection step of detecting Doppler signals at a desired range gate position, from reception signals obtained by transmitting and receiving ultrasounds to and from a patient; a measurement step of measuring a plurality of Doppler spectra in time series, for the Doppler signals detected at the detection step; a first image data generation step of generating first Doppler spectral image data by performing average processes for spectral components in the Doppler spectra measured at the measurement step; a second image data generation step of generating second Doppler spectral image data by selecting the spectral components of large power values on the basis of a preset threshold value, from among the spectral components in the Doppler spectra measured at the measurement step, and performing component processing of the selected spectral components and mean spectral components in the first Doppler spectral image data corresponding to the selected spectral components; and a display step of displaying the second Doppler spectral image data.

Besides, in order to solve the problems, the image data generation method according to the invention comprises a detection step of detecting Doppler signals at a desired range gate position, from reception signals obtained by transmitting and receiving ultrasounds to and from a patient; a measurement step of measuring a plurality of Doppler spectra in time series, for the Doppler signals detected at the detection step; a first average process step of generating first mean spectral components by performing first average processes for spectral components in the Doppler spectra measured at the measurement step; a first average process step of generating second mean spectral components by performing average processes which have an average interval shorter than that of the average processes at the first average process step; a first image data generation step of generating first Doppler spectral image data on the basis of the first mean spectral components; a second image data generation step of generating second Doppler spectral image data by selecting the mean spectral components of large power values on the basis of a preset threshold value, from among the second mean spectral components, and performing component processing of the selected mean spectral components and the first mean spectral components corresponding to the selected mean spectral components; and a display step of displaying the second Doppler spectral image data.

According to the invention, in a Doppler spectral image, discontinuities in spectral components of small power values susceptible to interference noise can be improved, and variations in a time direction or a frequency direction can be clearly displayed in spectral components of comparatively large power values.

BRIEF DESCRIPTION OF THE DRAWINGS

In the accompanying drawings:

FIG. 4 is a time chart showing the basic operations of a Doppler spectrum measurement unit in the embodiment;

FIGS. 5A and 5B are diagrams showing an FFT analysis method in an FFT analyzer in the embodiment, in which FIG. 5A shows discrete Doppler signals, while FIG. 5B shows spectral components;

FIG. 8 is a flow chart showing the steps of generating Doppler spectral image data in the embodiment;

FIGS. 9A and 9B are graphs showing Doppler spectra obtained by the embodiment, in which FIG. 9A shows the Doppler spectrum at an input node, while FIG. 9B shows the Doppler spectrum at an output node.

DETAILED DESCRIPTION OF THE PREFERRED EMBODIMENTS (Configuration of Equipment)

An embodiment of the present invention to be described here features that, in a Doppler spectral image which has been obtained through the FFT analysis of Doppler signals acquired from a patient, any spectral component smaller than a preset threshold value is displayed after performing a moving average process, whereas any spectral component equal to or larger than the threshold value is displayed without performing the moving average process.

Hereinbelow, the configuration of an ultrasonic Doppler diagnostic equipment in the embodiment in which the invention is applied to a sector scan scheme will be described with reference to FIGS. 2 through 6. Incidentally, FIG. 2 is a block diagram showing the general configuration of the ultrasonic Doppler diagnostic equipment in the embodiment, while FIG. 3 is a block diagram showing a transmission/reception unit and a data processing unit which constitute the ultrasonic Doppler diagnostic equipment.

Figure 1:
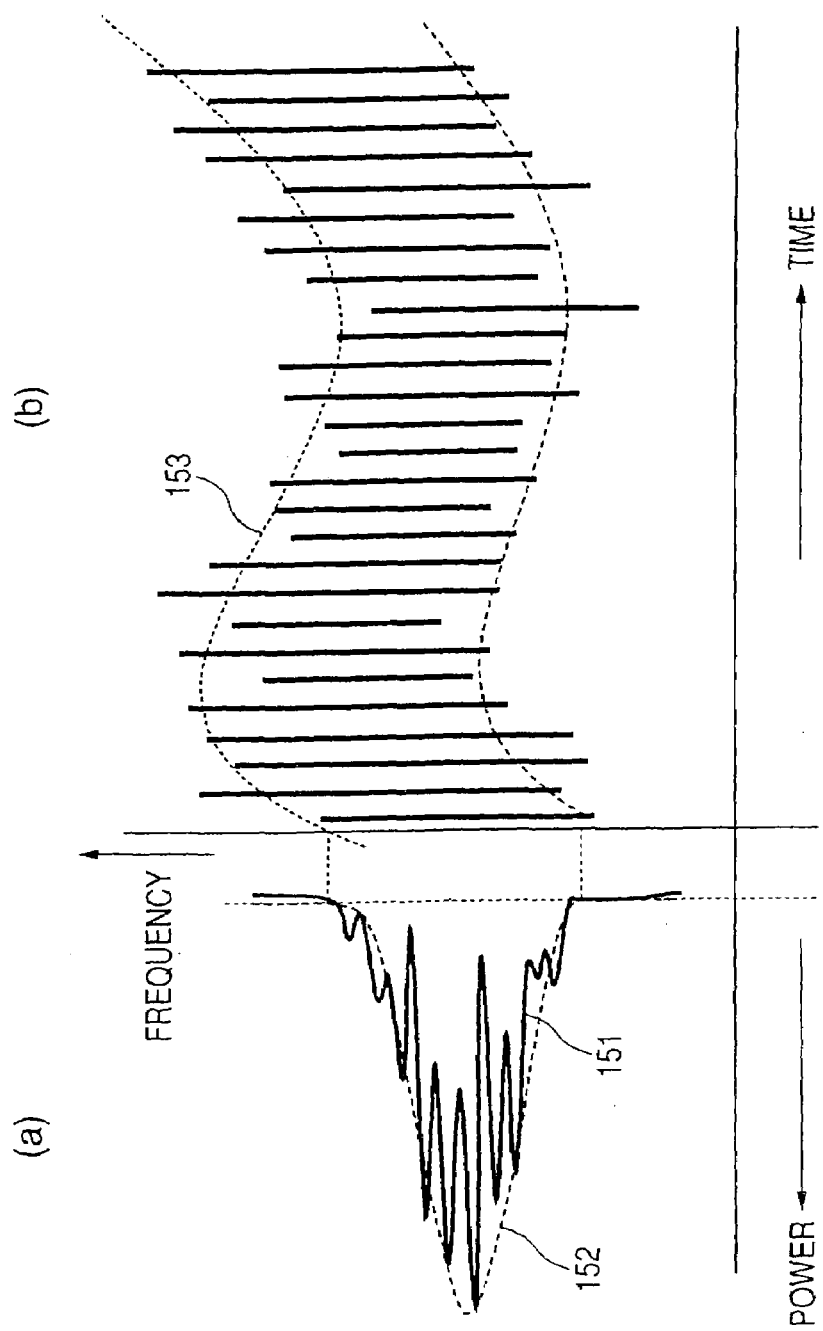
FIG. 1 is a graph showing the problems of a Doppler spectral image obtained by a prior-art method.
Figure 2:
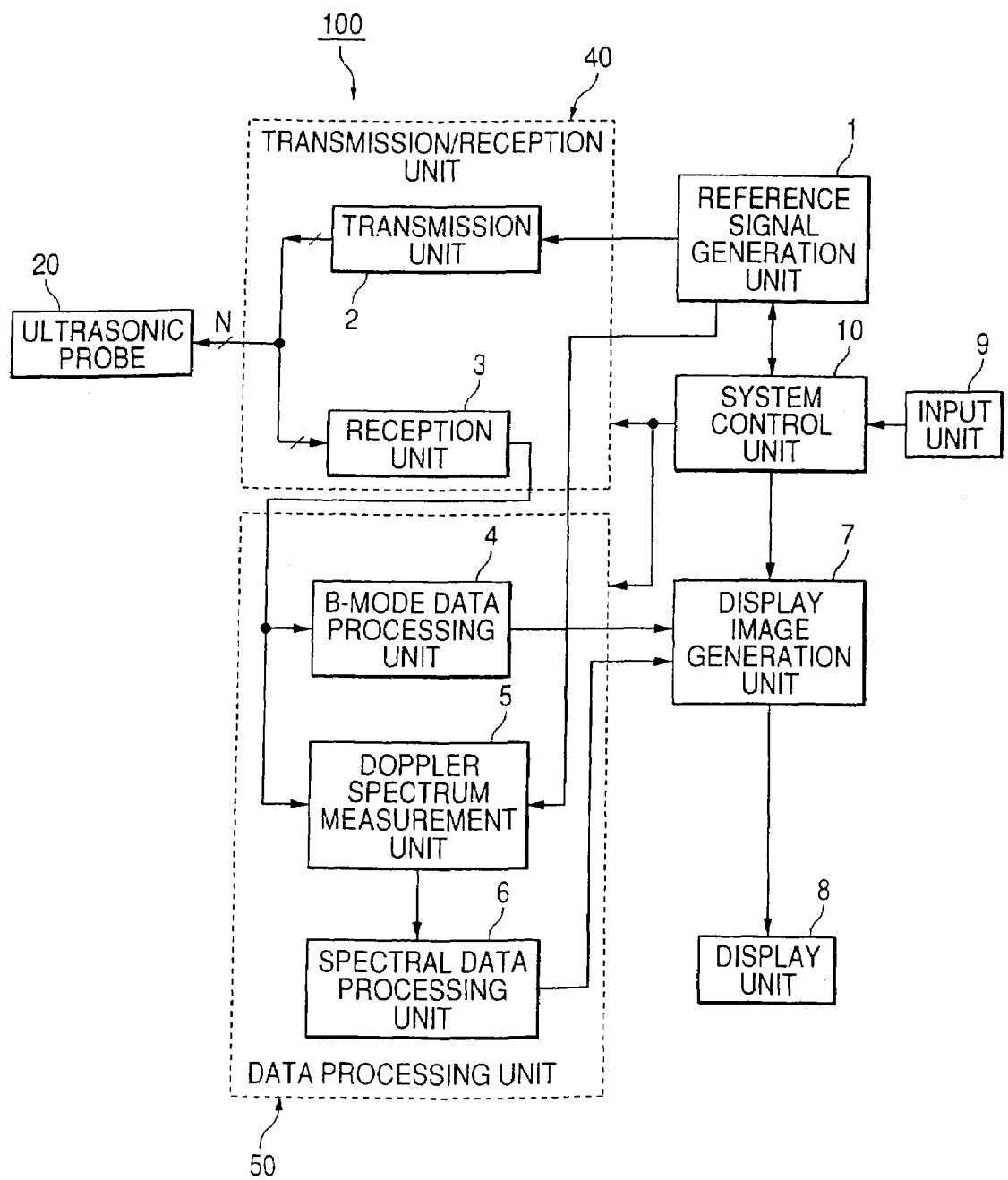
FIG. 2 is a block diagram showing the general configuration of an ultrasonic Doppler diagnostic equipment in an embodiment of the present invention.
Figure 3:
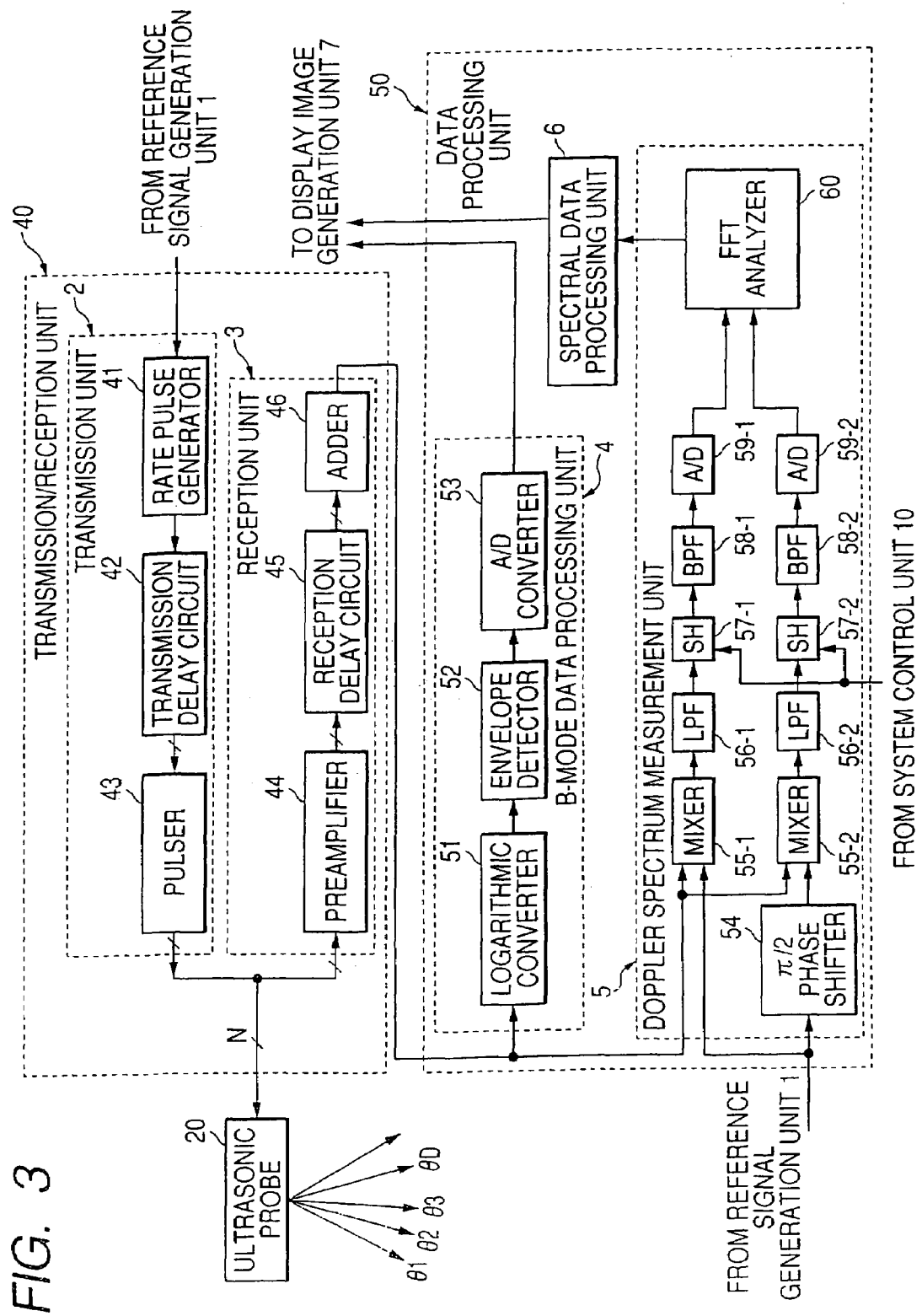
FIG. 3 is a block diagram showing the configurations of a transmission/reception unit and a data processing unit in the embodiment.

The ultrasonic Doppler diagnostic equipment 100 shown in FIG. 2 includes an ultrasonic probe 20 which transmits and receives ultrasounds to and from a patient, a transmission/reception unit 40 which transmits and receives electric signals to and from the ultrasonic probe 20, a data processing unit 50 which performs signal processing for obtaining B-mode data and a Doppler spectrum from the reception signals delivered from the transmission/reception unit 40, a display image generation unit 7 which saves the B-mode data and the Doppler spectrum obtained in the data processing unit 50 and which generates B-mode image data and Doppler spectral image data, and a display unit 8 which displays the image data.

Further, the ultrasonic Doppler diagnostic equipment 100 includes a reference signal generation unit 1 which generates, for example, a continuous wave or a rectangular wave having a frequency substantially equal to the center frequency (fo) of ultrasonic pulses, for the transmission/reception unit 40 or the data processing unit 50, an input unit 9 through which patient information, image display modes, ultrasonic data collection conditions, various command signals, etc. are inputted by an operator, and a system control unit 10 which generally controls the various units of the ultrasonic Doppler diagnostic equipment 100.

The ultrasonic probe 20 transmits and receives the ultrasounds in a state where its front face is held in touch with the surface of the patient, and it has a plurality of (N) minute piezoelectric transducers arrayed unidimensionally, at its front end part. Each of the piezoelectric transducers is an electroacoustic transducer, which has the functions of converting an electric pulse into an ultrasonic pulse (transmission ultrasound) in a transmission mode and converting an ultrasonic reflected wave (reception ultrasound) into an electric signal (reception signal) in a reception mode. That center frequency (fo) of the ultrasonic pulses which exerts great influence on the resolution and sensitivity of an ultrasonic image, is substantially determined by the thickness of each piezoelectric transducer. The ultrasonic probe 20 is constructed to be small in size and light in weight, and it is connected to the transmission unit 2 and reception unit 3 of the transmission/reception unit 40 through a cable. The ultrasonic probe 20 includes types corresponding to sector scan, linear scan, convex scan, etc., and any of the types is selected optionally in accordance with a part to-be-diagnosed. In the ensuing description, there will be mentioned a case of employing the ultrasonic probe 20 of the type corresponding to the sector scan, for the purpose of diagnosing the heart.

Next, the transmission/reception unit 40 shown in FIG. 3 includes the transmission unit 2 which generates drive signals for radiating transmission ultrasounds from the ultrasonic probe 20, and the reception unit 3 which receives reception ultrasounds from within the patient. The transmission unit 2 includes a rate pulse generator 41, a transmission delay circuit 42 and a pulser 43. Herein, the rate pulse generator 41 generates rate pulses for determining the repetition period (Tr) of the transmission ultrasounds to be radiated into the patient, by dividing the frequency of the continuous wave or rectangular wave fed from the reference signal generator 1, and it feeds the generated rate pulses to the transmission delay circuit 42.

Besides, the transmission delay circuit 42 is configured of the same number (N channels) of independent delay circuits as that of the piezoelectric transducers for the transmissions. This transmission delay circuit 42 gives the rate pulses delay times for focusing the transmission ultrasounds to predetermined depths in order to attain a fine beam width in the transmissions, and delay times for radiating the transmission ultrasounds in predetermined directions, whereupon it feeds the resulting rate pulses to the pulser 43. Further, likewise to the transmission delay circuit 42, the pulser 43 has the same number (N channels) of independent drive circuits as that of the piezoelectric transducers for the transmissions, and it generates drive pulses for driving the piezoelectric transducers built in the ultrasonic probe 20.

On the other hand, the reception unit 3 includes a preamplifier 44, a reception delay circuit 45 and an adder 46. The preamplifier 44 amplifies minute electric signals (reception signals) converted by the piezoelectric transducers, thereby to ensure a satisfactory S/N ratio. Besides, the reception delay circuit 45 gives the outputs of the preamplifier 44 delay times for focusing the reception ultrasounds from predetermined depths in order to attain a fine reception beam width, and delay times for setting intense reception directivities for the reception ultrasounds from predetermined directions. Subsequently, those outputs of the reception delay circuit 45 which have the predetermined delay times are sent to the adder 46 and are added up in this adder 46.

Next, the data processing unit 50 in FIG. 3 includes a B-mode data processing unit 4 which generates B-mode data for the reception signal outputted from the adder 46 of the reception unit 3, a Doppler spectrum measurement unit 5 which measures the frequency spectrum of Doppler signals contained in the reception signal, and a spectral data processing unit 6 which subjects the measured Doppler spectrum to signal processing such as a moving average process.

Herein, the B-mode data processing unit 4 includes a logarithmic converter 51, an envelope detector 52 and an A/D converter 53. The input signal of the B-mode data processing unit 4, that is, the reception signal outputted from the adder 46 of the reception unit 3 has its amplitude logarithmically converted in the logarithmic converter 51 so as to relatively emphasize weak signal components. Subsequently, the envelope detector 52 performs envelope detection for the reception signal after the logarithmic conversion, thereby to remove ultrasonic frequency components and to detect only amplitude information. Further, the A/D converter 53 subjects the output signal of the envelope detector 52 to A/D conversion, thereby to generate B-mode data.

On the other hand, the Doppler spectrum measurement unit 5 includes a $\pi/2$ phase shifter 54, mixers 55-1 and 55-2, LPFs (low-pass filters) 56-1 and 56-2, and SHs (sample-and-hold circuits) 57-1 and 57-2, and it further includes BPFs (band-pass filters) 58-1 and 58-2, A/D converters 59-1 and 59-2, and an FFT (Fast-Fourier-Transform) analyzer 60. Thus, the measurement unit 5 performs orthogonal phase detection for the reception signal fed from the reception unit 3 of the transmission/reception unit 40, thereby to detect the Doppler signals and to perform an FFT analysis for the Doppler signals obtained.

Next, the configuration and basic operations of the Doppler spectrum measurement unit 5 will be described in more detail by referring also to the time chart of FIG. 4. The reception signal ((c) in FIG. 4) is inputted to the first input terminals of the mixers 55-1 and 55-2 of the Doppler spectrum measurement unit 5. On the other hand, that reference signal ((a) in FIG. 4) of the reference signal generation unit 1 which has the frequency (fo) substantially equal to the center frequency of the reception signal is directly fed to the second input terminal of the mixer 55-1, and the reference signal with its phase shifted 90 degrees through the $\pi/2$ phase shifter 54 is sent to the second input node of the mixer 55-2. Besides, multiplication outputs based on the mixers 55-1 and 55-2 are respectively sent to the LPFs 56-1 and 56-2, so as to remove the components (components near 2fo) of the sum between the frequency of the input signal (reception signal) of the Doppler spectrum measurement unit 5 and the frequency (fo) of the reference signal fed from the reference signal generation unit 1, and to extract only the components (components near zero frequency) of the difference as Doppler signals ((d) in FIG. 4).

Subsequently, the SHs 57-1 and 57-2 are respectively fed with the Doppler signals outputted from the LPFs 56-1 and 56-2, and sampling pulses (range gate pulses) which the system control unit 10 has generated by dividing the frequency of the reference signal of the reference signal generation unit 1 ((e) in FIG. 4), thereby to sample and hold only the Doppler signals from distances designated by the sampling pulses ((f) in FIG. 4). Incidentally, the sampling pulses are generated a predetermined time period (Ts) after rate pulses ((b) in FIG. 4) indicative of timings at which transmission ultrasounds are radiated, and the generation timings are set at will by the operator of the input unit 9.

That is, the operator is permitted to detect the Doppler signals at a desired distance Lg from the ultrasonic probe 20, by altering the delay time Ts. Incidentally, the rate pulses having the period Tr are synchronous with the reference signal, and they are usually generated by dividing the frequency of the reference signal. Besides, the delay time Ts and the desired distance Lg have the relationship of 2Lg/C=Ts where C denotes a sound velocity through the patient.

Subsequently, stepped noise components superposed on the Doppler signals at the desired distance Lg as have been outputted from the SHs 57-1 and 57-2 are respectively removed by the BPFs 58-1 and 58-2 ((g) in FIG. 4). Further, the smoothed Doppler signals are respectively converted into digital signals by the A/D converters 59-1 and 59-2, and the digital signals are respectively fed to the FFT analyzer 60 so as to measure a frequency spectrum (termed "Doppler spectrum" below).

The FFT analyzer 60 includes an arithmetic circuit and a storage circuit, not shown. The storage circuit saves the Doppler signals outputted from the respective A/D converters 59-1 and 59-2, and the arithmetic circuit makes FFT analyses in the predetermined intervals of the series of Doppler signals saved in the storage circuit.

Figure 5A:
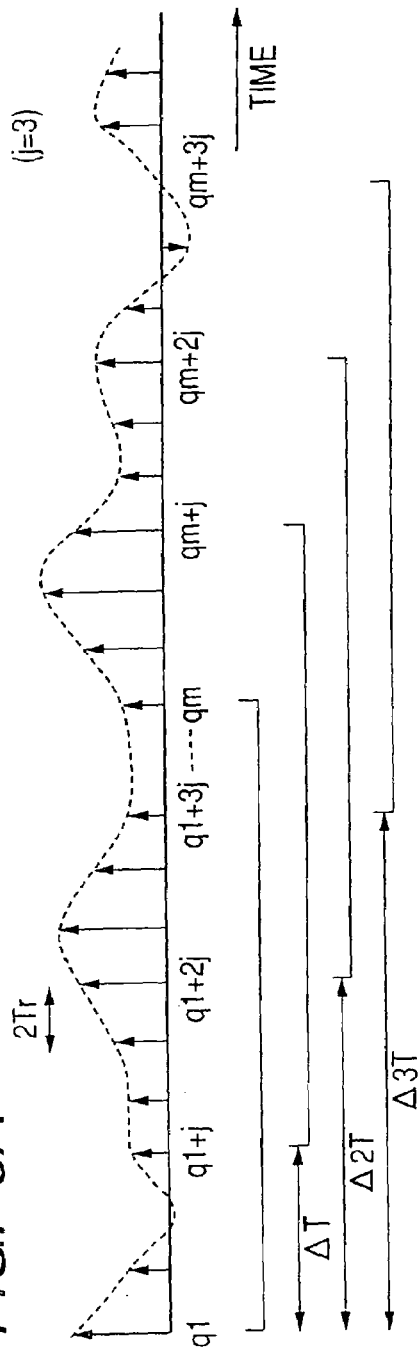
Figure 5B:
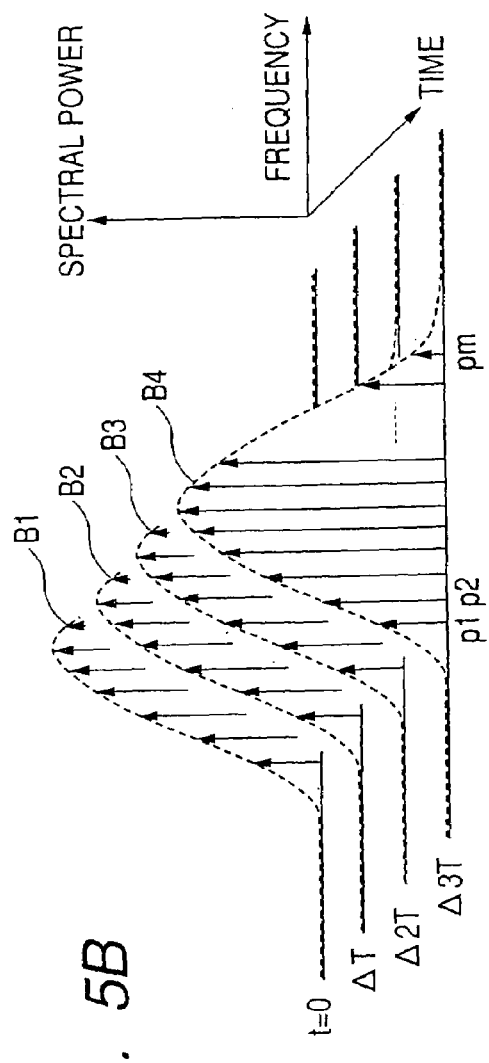

FIGS. 5A and 5B show an FFT analysis method in the FFT analyzer 60. An FFT analysis is made for, for example, m Doppler signals q1 through qm, among discrete Doppler signals (FIG. 5A) outputted from the A/D converters 59-1 and 59-2 of the Doppler spectrum measurement unit 5, whereby the spectral components p1 through pm of a first Doppler spectrum B1 are measured. Subsequently, m Doppler signals q1+j through qm+j after a time period $\Delta T$ are subjected to an FFT analysis, whereby the spectral components p1 through pm of a new Doppler spectrum B2 are measured.

Herein, a case of j=3 is illustrated in FIG. 5A. Thenceforth, m Doppler signals q1+2j through qm+2j after a time period $2\Delta T$, q1+3j through qm+3j after a time period $3\Delta T$, . . . are similarly subjected to FFT analyses in succession, whereby the spectral components p1 through pm of Doppler spectra B3 and B4 are respectively calculated (FIG. 5B).

Next, the configuration and basic operations of the spectral data processing unit 6 in the data processing unit 50 will be described with reference to the block diagram of FIG. 6. The spectral data processing unit 6 includes weighted-delay addition circuits 61-1 through 61-m which execute the moving average processes of the spectral components p1 through pm in the time direction, on the basis of the Doppler spectra B1, B2, . . . of the Doppler signals as are successively measured at the intervals of the time period $\Delta T$ and as already shown in FIG. 5B, a factor setting circuit 62 which sets weighting factors in the weighted-delay addition circuits 61-1 through 61-m, and a threshold setting circuit 63 which sets the range (threshold value) of the power values of the spectra for applying the moving average processes thereto by the weighted-delay addition circuits 61-1 through 61-m.

Herein, the weighted-delay addition circuits 61-1 through 61-m of m channels constitute an FIR (Finite Impulse Response) filter. Each of the weighted-delay addition circuits 61 includes a delay circuit 64 in which delay elements 74-1 through 74-r each having the delay time $\Delta T$ are connected in series, a weighting circuit 65 which has amplifiers 75-1 through 75-(r+1) for weighting the output signals of the delay elements 74-1 through 74-r at gains K0 through Kr, an addition circuit 66 which adds up the outputs of the amplifiers 75-1 through 75-(r+1) of (r+1) channels, and a synthesis circuit 67 which replaces or synthesizes the input signal of the weighted-delay addition circuit 61 and the output signal of the addition circuit 66.

Besides, the factor setting circuit 62 sets the gains K0 through Kr of the amplifiers 75-1 through 75-(r+1) in the weighting circuits 65 of the weighted-delay addition circuits 61-1 through 61-m, on the basis of control signals from the system control unit 10. In this case, the number of stages of the delay circuit 64 is set, depending upon the degree of interference noise ascribable to the interference of ultrasounds. By way of example, in case of performing the moving average process of 4 stages, the gains K4 through Kr in the amplifiers 75-5 through 75-(r+1) of the weighting circuit 65 are set at zero. Incidentally, the control signals of the factor setting circuit 62 to be fed from the system control unit 10 may be automatically set by the system control unit 10 on the basis of ultrasonic data collection conditions such as the ultrasonic frequency and the range gate distance Lg which are used, but they can also be set on the basis of the measured result of the FFT analyzer 60 by the operator of the input unit 9.

On the other hand, the threshold setting circuit 63 sets a threshold value $\alpha$ in the case of directly displaying the Doppler spectra measured by the FFT analyzer 60, and in the case of displaying the Doppler spectra after the moving average processes. By way of example, in a case where the power values of the spectral components p1 through pm of the Doppler spectrum are smaller than the threshold value $\alpha$ set by the threshold setting circuit 63, Doppler spectral image data are generated by employing results obtained through the moving average processes by the weighted-delay addition circuits 61, and in a case where the power values are larger than the threshold value $\alpha$, Doppler spectral image data are generated by directly employing results calculated by the FFT analyzer 60.

Incidentally, just as in the case of the control signals of the factor setting circuit 62, the system control unit 10 may automatically set the threshold value $\alpha$ in the threshold setting circuit 63 on the basis of ultrasonic data collection conditions, but the operator of the input unit 9 can set the threshold value $\alpha$ while observing the measured results of the FFT analyzer 60 or a Doppler spectral image. Especially in the former, the threshold value $\alpha$ is appropriately set on the basis of the gain of the equipment, the number of the piezoelectric transducers and the reception area (reception aperture) of the ultrasonic probe 20 for use in the receptions, and so on.

Alternatively, the threshold value may well be obtained from the spectral data of noise regions detected from within the Doppler spectral image. By way of example, the threshold value can be obtained from a mean noise level which is evaluated in such a way that noise levels at respective time points are obtained by tentatively regarding the upper and lower 10 pixels of the Doppler spectral image as noise, and that the noise levels are averaged in the time direction. Further, the threshold value can be obtained from a mean noise level which is evaluated in such a way that the Doppler spectral image is divided into a blood flow region and a noise region by auto-tracing, that the levels of the noise region at respective time points are obtained, and that the noise levels are averaged in the time direction. When the values of a larger range are adopted in this manner, a more probable value can be obtained as the threshold value.

Referring back to FIG. 2, the display image generation unit 7 has the functions of generating and saving image data. It includes a first storage area where B-mode data which the B-mode data processing unit 4 of the data processing unit 50 has generated on the basis of reception signals obtained by successively altering ultrasonic transmission/reception directions are saved in two dimensions, so as to generate B-mode image data, and a second storage area where the Doppler spectra B1, B2, . . . which the spectral data processing unit 6 has generated are saved in time series, so as to generate Doppler spectral image data.

On the other hand, the input unit 9 includes input devices such as a display panel or keyboard and a track ball or mouse, on an operation panel. It is used for setting patient information, image display modes, ultrasonic data collection conditions, display conditions, a range gate position, the threshold value α of spectra, for tracing maximum frequency components in a Doppler spectral image, for inputting various command signals, and so forth.

Besides, the display unit 8 includes a displaying image memory, a conversion circuit and a monitor, not shown. The B-mode image data or Doppler spectral image data, characters indicating the ultrasonic data collection conditions inputted from the input unit 9, etc. are synthesized by the displaying image memory, they are subjected to D/A conversion and television format conversion in the conversion circuit, and they are thereafter displayed on the monitor such as a CRT or a liquid crystal panel. Incidentally, the B-mode image data or Doppler spectral image data saved in the display image generation unit 7 are displayed in parallel or in superposition, on the monitor of the display unit 8. Besides, on the monitor, the Doppler spectral image data which contain a Doppler spectrum being substantially inphase with the B-mode image data are displayed in real time, and that desired position in the patient from which Doppler signals are sampled, that is, the position of a range gate, is displayed on the B-mode image.

In addition, the system control unit 10 includes a CPU and a storage circuit, not shown. The setting values such as the patient information, image display modes, ultrasonic data collection conditions, display conditions, range gate position, and spectral threshold value α, which are inputted from the input unit 9 by the operator are saved in the storage circuit. On the other hand, the CPU generally performs the controls of the various units of the ultrasonic Doppler diagnostic equipment 100 and the control of the whole system on the basis of the information items inputted from the input unit 9. Besides, the CPU generates sampling pulses for setting the range gate position by dividing the frequency of a reference signal fed from the reference signal generation unit 1, and feeds the sampling pulses to the SHs (sample-and-hold circuits) 57.

By the way, in this embodiment, the spectral data processing unit 6 constructs a decision unit in the invention. Besides, in the spectral data processing unit 6, the weighted-delay addition circuits 61-1 through 61-m construct an average process unit and first and second average process units in the invention, and the threshold setting circuit 63 constructs a threshold setting unit. Also, the addition circuit 66 and synthesis circuit 67 in the spectral data processing unit 6, and the display image generation unit 7 construct an image data generation unit and first and second image data generation units according to the invention.

(Generation Steps for Image Data)

Next, the steps of generating B-mode image data and Doppler spectral image data in this embodiment will be described with reference to FIG. 2 through FIGS. 9A and 9B. Incidentally, FIG. 8 is a flow chart showing the steps of generating the Doppler spectral image data in this embodiment.

In advance of the collection of ultrasonic data, the operator sets patient information, image display modes, ultrasonic data collection conditions, display conditions, a spectral threshold value α, etc. by the input unit 9, and the setting information items are sent to and saved in the unshown storage circuit of the system control unit 10. In this embodiment, display modes for a B-mode image and a Doppler spectral image are selected as the image display modes. Further, ultrasonic transmission/reception directions (θD) and a range gate position Lg for collecting Doppler signals are initially set (step S1 in FIG. 8).

After the initial settings have ended, the operator fixes the front end (ultrasonic transmission/reception face) of the ultrasonic probe 20 to a predetermined position on the surface of the body of the patient, and ultrasounds are transmitted and received for B-mode data collection in the first ultrasonic transmission/reception direction (θ1 direction). More specifically, the rate pulse generator 41 in FIG. 3 divides the frequency of a reference signal fed from the reference signal generator 1, thereby to generate rate pulses which determine the repetition period Tr of ultrasonic pulses to be radiated into the patient, and it feeds the rate pulses to the transmission delay circuit 42.

The transmission delay circuit 42 includes substantially the same number (N channels) of independent delay circuits as that of the piezoelectric transducers for the transmissions. This transmission delay circuit 42 gives delay times for focusing the ultrasounds to predetermined depths in order to attain a fine beam width in the transmissions, and delay times for transmitting the ultrasounds in a predetermined direction (θ1), to the rate pulses received from the rate pulse generator 41, whereupon it feeds the resulting rate pulses to the pulser 43.

The pulser 43 which is configured of the independent drive circuits of N channels, drives the piezoelectric transducers built in the ultrasonic probe 20, owing to electric pulses (drive signals) generated by the drive of the rate pulses outputted from the transmission delay circuit 42, thereby to radiate the ultrasonic pulses (transmission ultrasounds) into the patient.

Some of the transmission ultrasounds radiated into the patient are reflected from a tissue or the interface between internal organs of different acoustic impedances. Also, the transmission ultrasounds are sometimes reflected by mobile reflectors such as the cardiac wall and blood corpuscles. In such a case, the ultrasonic frequency of the transmission ultrasounds undergoes a Doppler shift. Ultrasonic reflected waves (reception ultrasounds) reflected from the patient tissue are received by the same piezoelectric transducers as in the transmission mode, and are converted into electric signals (reception signals). The reception signals are amplified by the preamplifier 44 of N channels, and are sent to the reception delay circuit 45 having the same number of channels.

On the other hand, the reception delay circuit 45 gives delay times for focusing the ultrasounds from the predetermined depths in order to attain a fine beam width in the receptions, and delay times for receiving the ultrasonic beams with an intense reception directivity in the predetermined direction (θ1), to the reception signals from the preamplifier 44, whereupon it sends the resulting reception signals to the adder 46. Besides, the adder 46 adds up the plurality of reception signals inputted through the preamplifier 44 and the reception delay circuit 45, into a single reception signal, whereupon it feeds the single reception signal to the B-mode data processing unit 4.

Subsequently, the reception signal sent to the B-mode data processing unit 4 is subjected to logarithmic conversion, envelope detection and A/D conversion, and the resulting data are saved in the first storage area for the B-mode image data, in the display image generation unit 7 in FIG. 2.

When the ultrasonic transmissions/receptions for the B-mode data collection in the θ1 direction have ended owing to the above steps, ultrasounds are transmitted and received in the direction (θD) initially set for Doppler spectral data collection. Also in this case, owing to steps similar to those of the ultrasonic transmissions/receptions in the θ1 direction, the ultrasounds are transmitted and received in the θD direction, and a reception signal outputted from the adder 46 of the reception unit 3 is fed to the Doppler spectrum measurement unit 5.

Subsequently, the Doppler spectrum measurement unit 5 converts the output of the adder 46 into a complex signal (IQ signal) by orthogonal phase detection employing the mixer 55 and the LPF 56, so as to feed the complex signal to the SH 57. The sampling pulse corresponding to the range gate position Lg initially set is fed from the system control unit 10 to the SH 57, and the complex signal is sampled and held on the basis of the sampling pulse. Besides, the output of the SH 57 is smoothed in the BPF 58 and is thereafter converted into a digital signal by the A/D converter 59, whereupon the digital signal is once saved in the storage circuit of the FFT analyzer 60.

When the first ultrasonic transmissions/receptions in the θD direction have ended, similar steps are carried out for ultrasonic transmissions/receptions for the B-mode in a θ2(θ2=θ1+Δθ) direction, second ultrasonic transmissions/receptions for the Doppler mode in the θD direction, ultrasonic transmissions/receptions for the B-mode in a θ3 (θ3=θ1+2Δθ) direction, third ultrasonic transmissions/receptions for the Doppler mode in the θD direction, . . . . In this manner, in collecting the B-mode data, the two-dimensional ultrasonic transmissions/receptions are performed as the direction is successively altered every Δθ. The B-mode data obtained are saved in the first storage area of the display image generation unit 7, so as to generate the B-mode image data.

On the other hand, in collecting Doppler spectral data, a plurality of times of ultrasonic transmissions/receptions are performed in the identical direction (θD), and Doppler signals obtained are successively saved in the unshown storage circuit of the FFT analyzer 60 (step S2 in FIG. 8). Besides, the unshown arithmetic circuit of the FFT analyzer 60 sets intervals shifted every predetermined time period (ΔT), for the Doppler signals collected continuously, and it makes FFT analyses for the Doppler signals in these intervals, thereby to measure Doppler spectra (step S3 in FIG. 8).

More specifically, the arithmetic circuit of the FFT analyzer 60 makes the FFT analysis by reading out, for example, the m signal components q1 through qm, thereby to measure the Doppler spectrum B1 constituted by the spectral components p1 through pm, as regards the discrete Doppler signals which have been obtained at a period (2Tr) being double the rate pulse period as shown in FIG. 5A. Subsequently, the arithmetic circuit makes the FFT analysis for the m signal components q1+j through qm+j after the time period ΔT, thereby to calculate the Doppler spectrum B2. Likewise, the Doppler spectra B3, B4, . . . are measured by the FFT analyses for m signal components after a time period 2ΔT, a time period 3ΔT, . . . .

Figure 6:
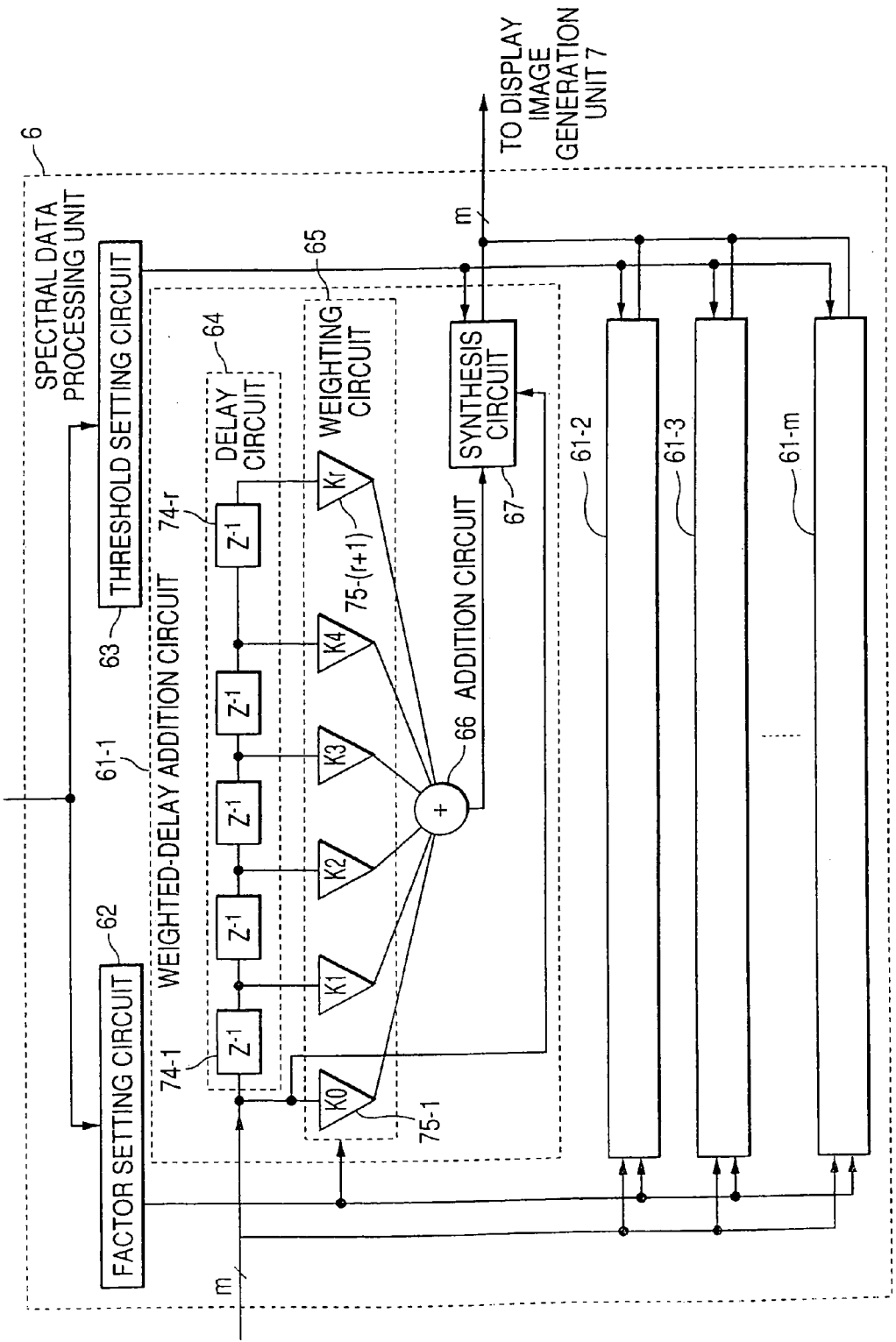
FIG. 6 is a block diagram showing the configuration of a spectral data processing unit in the embodiment.

Herein, the power values AP1 through APm of the m spectral components p1 through pm in the Doppler spectra of the Doppler signals measured at the intervals of the time period ΔT are successively fed to the input nodes of the weighted-delay addition circuits 61-1 through 61-m in the spectral data processing unit 6 shown in FIG. 6. By way of example, the weighted-delay addition circuit 61-1 is successively fed with the power values AP1(0), AP1(ΔT), AP1(2ΔT), . . . of the spectral components p1 in the Doppler spectra B1, B2, B3, corresponding to times t=0, ΔT, 2ΔT, . . . , and the weighted-delay addition circuit 61-m is successively fed with the power values APm(0), APm(ΔT), APm(2ΔT), . . . of the spectral components pm in the Doppler spectra B1, B2, B3, . . . corresponding to the times t=0, ΔT, 2ΔT, . . . . Accordingly, the output signal Y(t) of the addition circuit 66 of the weighted-delay addition circuit 61-1 becomes Y(0)=K0·AP1(0) at t=0, Y(ΔT)=K1·AP1(0)+K0·AP1(ΔT) at t=ΔT, Y(2ΔT)=K2·AP1(0)+K1·AP1(ΔT)+K0·AP1(2ΔT) at t=2ΔT, . . . . In this manner, a moving average process in the time direction is executed for the power values AP1 of the spectral components p1 measured at the intervals of the time period ΔT.

Likewise, moving average processes in the time direction are executed for the spectral components p2 through pm. Besides, Doppler spectral image data (termed "first Doppler spectral image data" below) generated by the moving average processes based on the Doppler spectra B1, B2, B3, . . . are fed to the input nodes of the synthesis circuits 67 and are once saved in the storage circuit thereof. On the other hand, the power values AP1 through APm of the spectral components of the Doppler spectra B1, B2, B3, are directly fed to the other input nodes of the synthesis circuits 67 (step S4 in FIG. 8).

Subsequently, in a case where the power values AP1 through APm of the Doppler spectra B1, B2, B3, . . . fed from the FFT analyzer 60 have values larger than a threshold value α previously set in the threshold setting circuit 63, the synthesis circuits 67 execute the replacement processes or synthesis processes between the power values AP1 through APm and the power values of the corresponding spectral components in the first Doppler spectral image data.

Doppler spectral image data (termed "second Doppler spectral image data" below) which have been generated anew in this manner by replacing or synthesizing the power values of the first Doppler spectral image data and the power values of the spectral components before the moving average processes on the basis of the threshold value α of the threshold setting circuit 63, are saved in the second storage area of the display image generation unit 7 (step S5 in FIG. 8).

The second Doppler spectral image data generated by the steps stated above are displayed on the display unit 8 alone or after being synthesized with the B-mode image data generated simultaneously. More specifically, the system control unit 10 reads out the B-mode image data saved in the first storage area of the display image generation unit 7 and the second Doppler spectral image data saved in the second storage area, and it superposes numerals, characters, etc. being attendant information, on the image data read out, so as to once save the resulting image data in the displaying image data storage circuit 61. Besides, the image data are fed to the conversion circuit and subjected to D/A conversion, TV format conversion, etc., so as to display the resulting image on the monitor of the display unit 8 (step S6 in FIG. 8).

Figure 7:
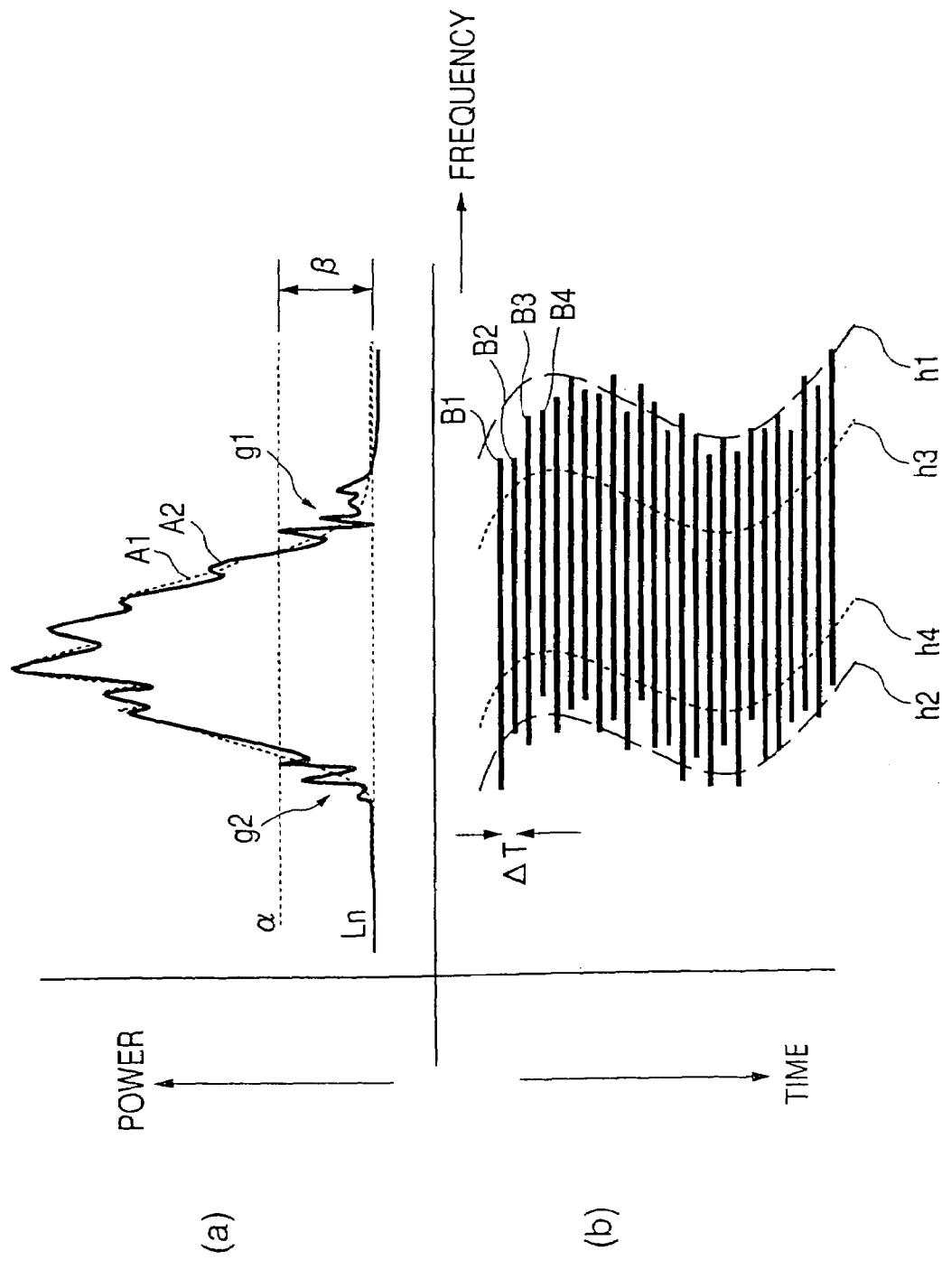
FIG. 7 is a diagram showing a Doppler spectral image obtained by the embodiment.

FIG. 7 schematically shows advantages which are attained by the embodiment. A curve A1 (broken line) on the upper side (a) of FIG. 7 indicates a true Doppler spectrum, while a curve A2 (solid line) indicates the measured values of a Doppler spectrum in which the influence of interference noise appeared in the vicinity g1 of a maximum frequency spectral component and the vicinity g2 of a minimum frequency spectral component, the components having comparatively small power values. On the other hand, the lower side (b) of FIG. 7 illustrates an example of a Doppler spectral image showing the variations of Doppler spectra in the direction of time. Herein, Doppler spectra B1, B2, B3, B4, . . . intensity-modulated by the power values of individual spectral components in the Doppler spectrum in FIG. 5A are arrayed in the direction of a time axis at intervals of a time period ΔT.

The measurement of a maximum spectral component (namely, maximum blood flow velocity) in the Doppler spectral image is very important in the quantitative analysis of a cardiac function, etc. Nevertheless, unevenness has appeared on account of the influence of the interference noise and has made the measurement difficult. However, in the first Doppler spectral image generated by the moving average processes in this embodiment, the measurement of a true maximum spectral component indicated by a curve h1 is facilitated.

Further, in a case where the power values of spectral components before the moving average processes are equal to or larger than a threshold value α which the threshold setting circuit 63 has set to be β higher than a system noise level Ln that is determined by ultrasonic data collection conditions such as the gain of the equipment and the aperture of the piezoelectric transducers, the second Doppler spectral image data are generated by replacing the power values of the first Doppler spectral image data with the equal or larger power values of the spectral components. Owing to the replacements, the power values before the moving average processes are employed in a region which is enclosed with curves h3 and h4. Thus, a subtle variation in the time direction or in a frequency direction can be clearly displayed according to the second Doppler spectral image data.

Figure 9A:
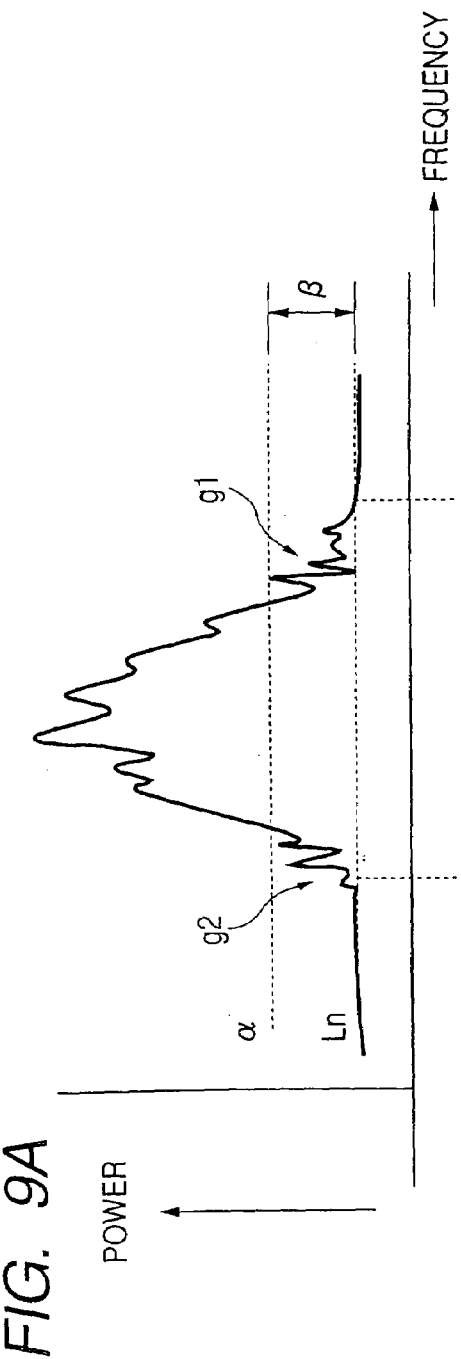
Figure 9B:
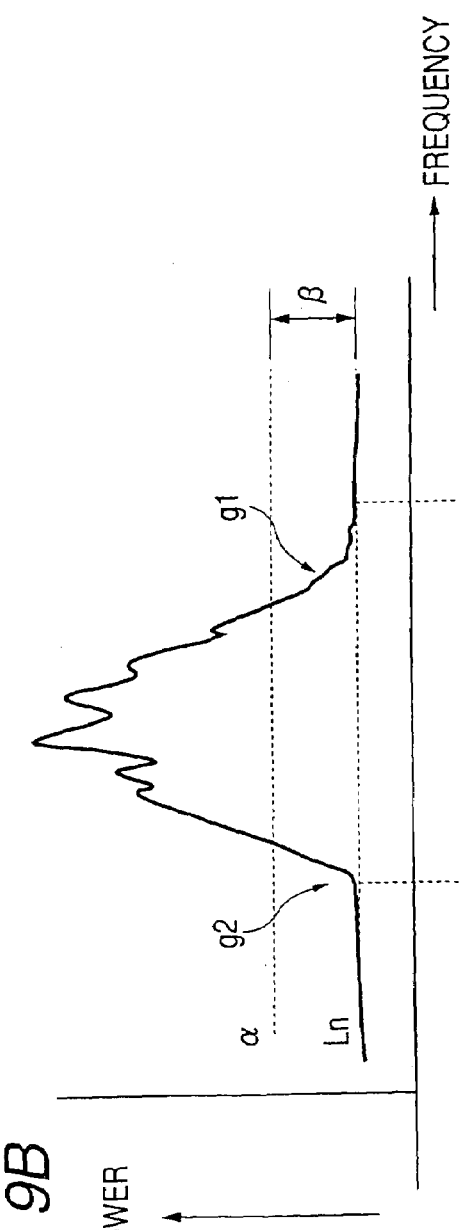

FIGS. 9A and 9B show the Doppler spectrum (FIG. 9A) at the input node of the spectral data processing unit 6, and the Doppler spectrum (FIG. 9B) at the output node thereof, respectively. The spectral components lower than the threshold value α, in the vicinity g1 of the maximum frequency component and the vicinity g2 of the minimum frequency component, have the interference noise removed by the moving average processes in the spectral data processing unit 6. In contrast, the spectral components equal to or higher than the threshold value α are not subjected to the moving average processes, so that the variations of the Doppler spectrum can be clearly observed.

As stated above, according to the embodiment, the Doppler spectral components smaller than the preset threshold value α are subjected to the moving average processes, and the Doppler spectral components equal to or larger than the threshold value α are displayed without performing the moving average processes, whereby the contours of edge parts in the Doppler spectral image can be displayed continuously and smoothly. Therefore, the automatic tracing or manual tracing of, for example, the maximum blood flow velocity can be performed precisely and easily. On the other hand, in the central region (for example, the interval h3-h4 in FIG. 7) of the Doppler spectral image, a high spatial resolution is exhibited, and hence, the subtle variations can be observed.

(Modified Embodiment)

Next, a modification of the spectral data processing unit 6 in this embodiment will be described with reference to the block diagram of FIG. 10. In the foregoing embodiment, in the Doppler spectrum obtained by making the FFT analysis for the Doppler signals acquired from the patient, only the spectral components smaller than the preset threshold value α are subjected to the moving average process. This modification features that even the spectral components whose power values are not smaller than the threshold value α are subjected to a moving average process of light degree.

Figure 10:
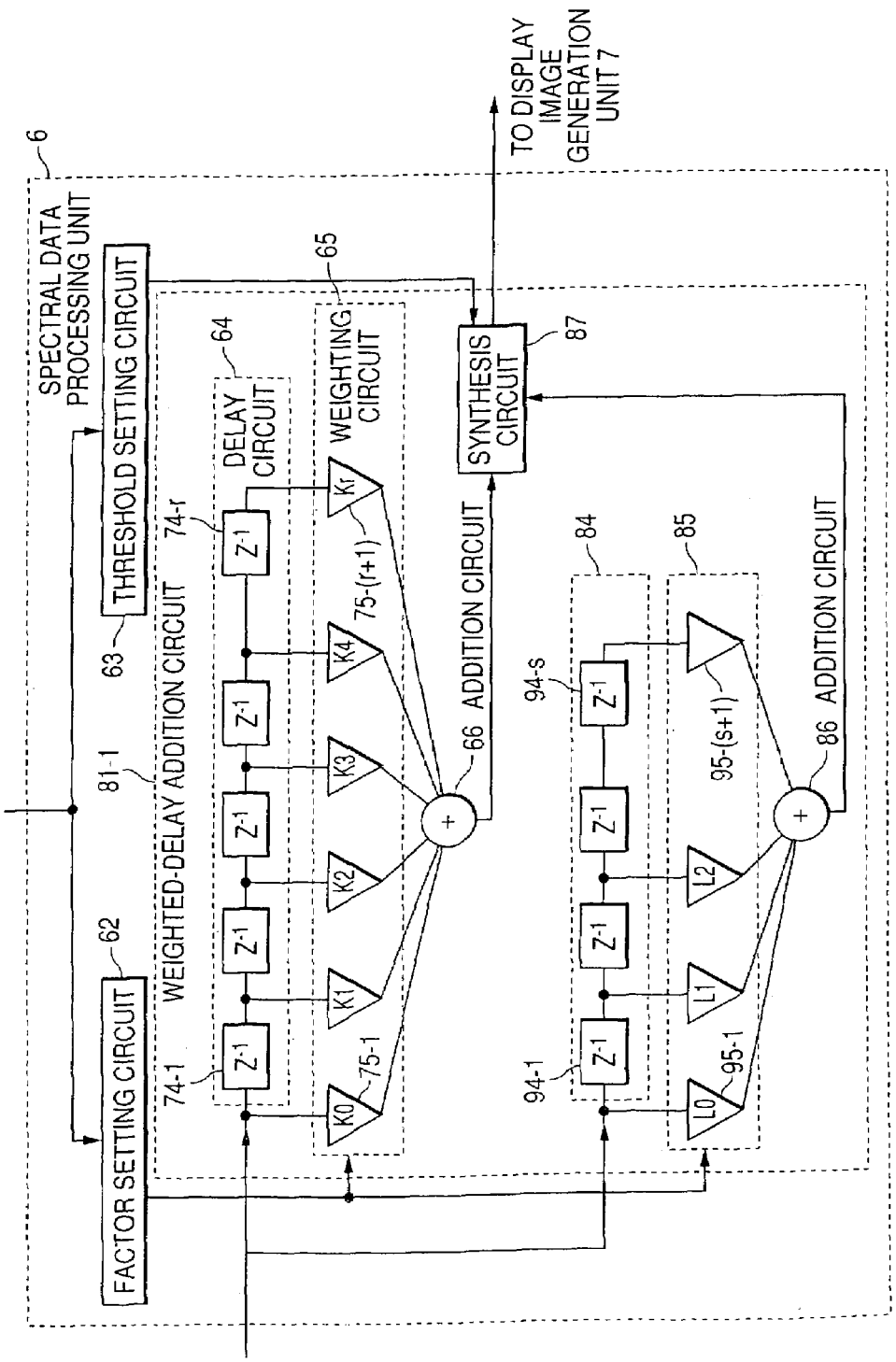
FIG. 10 is a block diagram showing the configuration of a spectral data processing unit in a modification to the embodiment.

FIG. 10 shows the weighted-delay addition circuit 81-1 of a spectral data processing unit 6 in the modification. Identical numerals and signs are assigned to units which have the same functions as in the weighted-delay addition circuit 61-1 in the foregoing embodiment shown in FIG. 6, and they shall be omitted from description.

The weighted-delay addition circuit 81-1 in FIG. 10 constructs two FIR filters. It has the first FIR filter including as in the foregoing embodiment, a delay circuit 64 in which delay elements 74-1 through 74-r each having a delay time AT are connected in series, a weighting circuit 65 which has amplifiers 75-1 through 75-(r+1) for weighting spectral components inputted to the input node of the delay element 74-1 and outputted from the output nodes of the delay elements 74-1 through 74-r, at gains K0 through Kr, and an addition circuit 66 which adds up the outputs of the amplifiers 75-1 through 75-(r+1) of (r+1) channels.

Further, the weighted-delay addition circuit 81-1 has the second FIR filter including a delay circuit 84 in which delay elements 94-1 through 94-s are connected in series, a weighting circuit 85 which has amplifiers 95-1 through 95-(s+1) for weighting the power values of spectral components inputted to the input node of the delay element 94-1 and outputted from the output nodes of the delay elements 94-1 through 94-s, at gains L0 through Ls, and an addition circuit 86 which adds up the outputs of the amplifiers 95-1 through 95-(s+1). It also has a synthesis circuit 87 which synthesizes the output of this second FIR filter and that of the above first FIR filter. Here, r>s holds, and the moving average interval of the second FIR filter is set to be smaller than that of the first FIR filter.

The input nodes of the first and second FIR filters which constitute the weighted-delay addition circuit 81-1 of the spectral data processing unit 6 shown in FIG. 10, are successively fed with the power values AP1(0), AP1(ΔT), AP1(2ΔT), ... of spectral components p1 in Doppler spectra B1, B2, B3, ... corresponding to times t=0, ΔT, 2ΔT, ..., so as to perform a moving average process. Also, similar moving average processes are performed for spectral components p2 through pm.

Besides, first Doppler spectral image data generated by the moving average processes of the first FIR filter, and second Doppler spectral image data generated by the moving average processes of the second FIR filter are fed to the synthesis circuit 87 and are once saved. Subsequently, the synthesis circuit 87 compares the power values of the spectral components constituting the second Doppler spectral image data, with a threshold value α set in a threshold setting circuit 63 beforehand, and it replaces or synthesizes the spectral components having the power values equal to or larger than the threshold value α, and the spectral components of the first Doppler spectral image data at corresponding parts.

According to the modification, the moving average interval of the second FIR filter is smaller than that of the first FIR filter. Therefore, interference noise mixed in the Doppler spectra having the power values equal to or larger than the threshold value α can be reduced, and moreover, the variations of the original Doppler spectra in a time direction and a frequency direction can be clearly displayed.

By the way, in the modification shown in FIG. 10, the first and second FIR filters are juxtaposed for the brevity of description, but it is also allowed, for example, to dispose only the first filter and to perform the above processing in time series. Besides, the threshold setting circuit 63 may well set a plurality of threshold values so as to replace or synthesize spectral components on the basis of the respective threshold values.

Although the present invention has thus far been described on the embodiments, it is not narrowly restricted to these embodiments, but it can be performed in altered forms. By way of example, although the moving average processes of the Doppler spectra in the embodiment or the modification have been performed in the direction of the time axis for the spectral components, they may well be performed in the direction of a frequency axis for the respective Doppler spectra, or they may well be performed in both the direction of the time axis and the direction of the frequency axis.

Further, each of the foregoing embodiments has been described on the method in which the second Doppler spectral image data are generated by replacing the first Doppler spectral image data after the moving average addition process, with the spectral components equal to or larger than the threshold value, but any other synthesis method may well be adopted.

Besides, although the method based on the ultrasonic data collection conditions has been mentioned for setting the system noise level, it is also allowed to detect a noise region from within a Doppler spectral image and to obtain the system noise level from the spectral data of the noise region. Alternatively, the operator may well set the system noise level on the basis of, for example, a B-mode image or the Doppler spectral image displayed on the display unit. Likewise, regarding the setting of the threshold value, the operator can set or update this parameter while observing the Doppler spectral image displayed on the display unit.

In addition, the range gate for determining the collection part of Doppler signals is not restricted to the single position, but Doppler spectral image data may well be generated on the basis of Doppler signals from a plurality of parts determined by a plurality of range gates. Besides, an ultrasonic image which is displayed simultaneously with the Doppler spectral image may well be a color Doppler image or the combination between the B-mode image and the color Doppler image.

What is claimed is:

1. An ultrasonic Doppler diagnostic equipment comprising;
   an ultrasonic probe which has piezoelectric transducers for transmitting and receiving ultrasound to and from a patient,
   a transmission/reception unit which transmits and receives electric signals to and from the piezoelectric transducers,
   a Doppler signal detection unit which detects Doppler signals at a desired range gate position, from the reception signals obtained by said transmission/reception unit,
   a spectrum measurement unit which measures a Doppler spectrum on the basis of the Doppler signals detected by said Doppler signal detection unit,
   a threshold value setting unit which sets a threshold value for power values of spectral components in the Doppler spectrum measured by said spectrum measurement unit,
   an average process unit which performs an average process for the spectral components of small power values selected on the basis of the threshold value set by said threshold value setting unit, from among the spectral components in the Doppler spectrum measured by said spectrum measurement unit,
   an image data generation unit which generates Doppler spectral image data through component processing of mean spectral components subjected to the average process by said average process unit and the spectral components of large power values not subjected to the average process, and
   a display unit which displays the Doppler spectral image data.

2. An ultrasonic Doppler diagnostic equipment as defined in claim 1, wherein said threshold value setting unit sets the threshold value for the power values of the spectral components in the Doppler spectrum, on the basis of ultrasonic data collection conditions.

3. An ultrasonic Doppler diagnostic equipment as defined in claim 2, wherein said threshold value setting unit sets the threshold value for the power values of the spectral components in the Doppler spectrum, on the basis of at least one of an equipment gain and an effective aperture of said ultrasonic probe.

4. An ultrasonic Doppler diagnostic equipment as defined in claim 1, wherein said threshold value setting unit detects a noise region from the Doppler spectral image data generated by the image data generation unit, and it sets the threshold value on the basis of spectral data of the noise region.

5. An ultrasonic Doppler diagnostic equipment as defined in claim 4, wherein said threshold value setting unit obtains a noise level by regarding a predetermined region of the Doppler spectral image as the noise region, and setting the threshold value from a mean noise level averaged in a time direction.

6. An ultrasonic Doppler diagnostic equipment as defined in claim 4, wherein said threshold value setting unit divides the Doppler spectral image into a blood flow region and a noise region by auto-tracing, obtains a level of the noise region, and setting the threshold value based on a mean noise level averaged in a time direction.

7. An ultrasonic Doppler diagnostic equipment comprising;
   an ultrasonic probe which has piezoelectric transducers for transmitting and receiving ultrasound to and from a patient,
   a transmission/reception unit which transmits and receives electric signals to and from the piezoelectric transducers,
   a Doppler signal detection unit which detects Doppler signals at a desired range gate position, from the reception signals obtained by said transmission/reception unit,
   a spectrum measurement unit which measures a Doppler spectrum on the basis of the Doppler signals detected by said Doppler signal detection unit,
   a threshold value setting unit which sets a threshold value for power values of spectral components in the Doppler spectrum measured by said spectrum measurement unit,
   an average process unit which performs an average process for the spectral components in the Doppler spectrum measured by said spectrum measurement unit,
   a first image data generation unit which generates first Doppler spectral image data by employing mean spectral components subjected to the average process by said average process unit,
   a second image data generation unit which generates second Doppler spectral image data by selecting the spectral components of large power values on the basis of the threshold value set by said threshold value setting unit, from among the spectral components in the Doppler spectrum measured by said spectrum measurement unit, and performing component processing of the selected spectral components and the mean spectral components of the first Doppler spectral image data corresponding to the selected spectral components, and
   a display unit which displays the second Doppler spectral image data.

8. An ultrasonic Doppler diagnostic equipment as defined in claim 7, wherein the processing in said second image data generation unit is one of replacement processing and weighted addition processing.

9. An ultrasonic Doppler diagnostic equipment comprising;
   an ultrasonic probe which has piezoelectric transducers for transmitting and receiving ultrasound to and from a patient,
   a transmission/reception unit which transmits and receives electric signals to and from the piezoelectric transducers,
   a Doppler signal detection unit which detects Doppler signals at a desired range gate position, from the reception signals obtained by said transmission/reception unit,
   a spectrum measurement unit which measures a Doppler spectrum on the basis of the Doppler signals detected by said Doppler signal detection unit, a threshold value setting unit which sets a threshold value for power values of spectral components in the Doppler spectrum measured by said spectrum measurement unit, a first average process unit which performs an average process for the spectral components in the Doppler spectrum measured by said spectrum measurement unit, a first image data generation unit which generates first Doppler spectral image data by employing first mean spectral components subjected to the average process by said first average process unit, a second average process unit which performs an average process having an average interval shorter than that of the average process based on said first average process unit, for the spectral components in the Doppler spectrum measured by said spectrum measurement unit, a second image data generation unit which generates second Doppler spectral image data by selecting second mean spectral components of large power values on the basis of the threshold value set by said threshold value setting unit, from among the second mean spectral components subjected to the average process by said second average process unit, and performing component processing of the selected second mean spectral components and the first mean spectral components of the first Doppler spectral image data corresponding to the second mean spectral components, and a display unit which displays the second Doppler spectral image data.

10. An ultrasonic Doppler diagnostic equipment as defined in claim 9, wherein said first average process unit and said second average process unit subject the first spectral components and the second spectral components to moving average processes in at least one of a time axis direction and a frequency direction, respectively.

11. An image data generation method comprising;

a detection step of detecting Doppler signals at a desired range gate position from reception signals obtained by transmitting and receiving ultrasounds to and from a patient, a measurement step of measuring a plurality of Doppler spectra in a time series, of the Doppler signals detected at said detection step, a first image data generation step of generating first Doppler spectral image data by performing average processes for spectral components in the Doppler spectra measured at said measurement step, a second image data generation step of generating second Doppler spectral image data by selecting the spectral components of large power values on the basis of a preset threshold value, from among the spectral components in the Doppler spectra measured at said measurement step, and performing component processing of the selected spectral components and mean spectral components in the first Doppler spectral image data corresponding to the selected spectral components, and a display step of displaying the second Doppler spectral image data.

12. An image data generation method comprising;

a detection step of detecting Doppler signals at a desired range gate position, from reception signals obtained by transmitting and receiving ultrasounds to and from a patient, a measurement step of measuring a plurality of Doppler spectra in a time series, of the Doppler signals detected at said detection step, a first average process step of generating first mean spectral components by performing first average processes for spectral components in the Doppler spectra measured at said measurement step, a second average process step of generating second mean spectral components by performing average processes which have an average interval shorter than an average interval at the first average processes, a first image data generation step of generating first Doppler spectral image data on the basis of the first mean spectral components, a second image data generation step of generating second Doppler spectral image data by selecting the mean spectral components of large power values on the basis of a preset threshold value, from among the second mean spectral components, and performing component processing of the selected mean spectral components and the first mean spectral components corresponding to the selected mean spectral components, and a display step of displaying the second Doppler spectral image data.

* * * * *